(12) United States Patent
Naqvi

(10) Patent No.: US 12,396,930 B2
(45) Date of Patent: Aug. 26, 2025

(54) STABLE ANHYDROUS FOAMING AND GELLING HAND SOAP CONCENTRATE AND METHOD OF MAKING SAME

(71) Applicant: ONE HOME BRANDS, INC., New York, NY (US)

(72) Inventor: Syed Humza Naqvi, Walnut Creek, CA (US)

(73) Assignee: One Home Brands, Inc., New York, NY (US)

( * ) Notice: Subject to any disclaimer, the term of this patent is extended or adjusted under 35 U.S.C. 154(b) by 0 days.

(21) Appl. No.: 16/796,438

(22) Filed: Feb. 20, 2020

(65) Prior Publication Data
US 2020/0261327 A1 Aug. 20, 2020

Related U.S. Application Data

(60) Provisional application No. 62/889,480, filed on Aug. 20, 2019, provisional application No. 62/808,021, filed on Feb. 20, 2019.

(51) Int. Cl.
A61K 8/00 (2006.01)
A61K 8/02 (2006.01)
A61K 8/19 (2006.01)
A61K 8/34 (2006.01)
A61K 8/36 (2006.01)
A61K 8/365 (2006.01)
A61K 8/368 (2006.01)
A61K 8/46 (2006.01)
A61K 8/73 (2006.01)
A61K 8/86 (2006.01)
A61K 8/9789 (2017.01)
A61Q 19/10 (2006.01)

(52) U.S. Cl.
CPC .............. A61K 8/0216 (2013.01); A61K 8/19 (2013.01); A61K 8/342 (2013.01); A61K 8/345 (2013.01); A61K 8/361 (2013.01); A61K 8/365 (2013.01); A61K 8/368 (2013.01); A61K 8/463 (2013.01); A61K 8/733 (2013.01); A61K 8/86 (2013.01); A61K 8/9789 (2017.08); A61Q 19/10 (2013.01)

(58) Field of Classification Search
CPC .. C11D 17/0073; A61K 8/0216; A61K 8/361; A61K 8/00; A61Q 19/10
See application file for complete search history.

(56) References Cited

U.S. PATENT DOCUMENTS

| 5,336,500 A * | 8/1994 | Richter ................ C11D 3/2075 424/405 |
| 5,505,938 A | 4/1996 | Pocalyko et al. |
| 5,741,520 A | 4/1998 | Desenna |
| 5,817,337 A | 10/1998 | Desenna |
| 5,958,454 A | 9/1999 | Schrempf et al. |
| 6,099,861 A * | 8/2000 | DeSenna ................ A01N 59/00 424/465 |
| 6,310,014 B1 * | 10/2001 | Rau ........................ C11D 3/221 510/276 |
| 6,645,474 B1 * | 11/2003 | Galdi .................... A61K 8/463 424/59 |
| 6,713,441 B1 | 3/2004 | DeSenna et al. |
| 7,163,692 B2 | 1/2007 | Lagatol |
| 11,401,488 B2 | 8/2022 | Naqvi |
| 11,517,512 B2 * | 12/2022 | Jaracz .................. A61K 8/4973 |
| 2003/0003136 A1 | 1/2003 | Bergquist |
| 2003/0199077 A1 | 10/2003 | Fano et al. |
| 2004/0058843 A1 | 3/2004 | Del Nunzio et al. |
| 2004/0126411 A1 | 7/2004 | Lagatol et al. |
| 2004/0127385 A1 * | 7/2004 | O'Neil ..................... C11D 3/48 510/438 |
| 2004/0127388 A1 | 7/2004 | Del Nunzio et al. |
| 2005/0197275 A1 | 9/2005 | Hsu et al. |
| 2005/0250667 A1 * | 11/2005 | Quellet ................ C11D 3/0052 510/444 |
| 2005/0288208 A1 | 12/2005 | Keenan |
| 2006/0205626 A1 | 9/2006 | Gant |
| 2008/0096784 A1 | 4/2008 | Barg |
| 2009/0150111 A1 | 6/2009 | Riegel et al. |
| 2009/0169500 A1 * | 7/2009 | Sunkara ................. A61Q 19/00 424/65 |
| 2010/0267599 A1 | 10/2010 | Lucka et al. |
| 2011/0039744 A1 | 2/2011 | Heath et al. |
| 2011/0105375 A1 | 5/2011 | Myers et al. |
| 2013/0338053 A1 | 12/2013 | Casco |
| 2014/0174467 A1 | 6/2014 | Larson, III et al. |
| 2015/0366764 A1 * | 12/2015 | Batton ................... A61K 8/361 424/43 |
| 2016/0000848 A1 | 1/2016 | Koganov et al. |
| 2017/0172880 A1 | 6/2017 | Lavender et al. |

(Continued)

FOREIGN PATENT DOCUMENTS

CN 1220306 A 6/1999
CN 103194330 A 7/2013

(Continued)

OTHER PUBLICATIONS

Combined Search and Examination Report issued May 19, 2020 in British Application No. 2002371.9.
Search Report mailed May 19, 2020 in British Application No. 2002371.9.
International Search Report and Written Opinion mailed May 29, 2020 in International Application No. PCT/US2020/019061.
International Search Report and Written Opinion mailed Sep. 2, 2020 in International Application No. PCT/US2020/019058.
Examination report issued in corresponding AU Application No. 2020226741, dated Nov. 30, 2021.
Examination report issued in corresponding AU Application No. 2020225452, dated Dec. 1, 2021.

(Continued)

Primary Examiner — Necholus Ogden, Jr.
(74) Attorney, Agent, or Firm — Herbert Smith Freehills Kramer (US) LLP

(57) ABSTRACT

The invention relates to stable, anhydrous foaming hand soap concentrated formulation in solid forms.

22 Claims, No Drawings

(56) References Cited

U.S. PATENT DOCUMENTS

| | | | |
|---|---|---|---|
| 2018/0092357 | A1 | 4/2018 | Premachandran et al. |
| 2018/0105766 | A1 | 4/2018 | Casco |
| 2020/0010402 | A1 | 1/2020 | Chandrasekaran |
| 2021/0009922 | A1 | 1/2021 | Klingman et al. |
| 2021/0171865 | A1 | 6/2021 | Pambou |
| 2022/0202730 | A1 | 6/2022 | Basit et al. |

FOREIGN PATENT DOCUMENTS

| | | | | |
|---|---|---|---|---|
| CN | 105454291 | A | | 4/2016 |
| CN | 106635474 | A | | 5/2017 |
| CN | 106753932 | A | * | 5/2017 |
| CN | 107384602 | A | | 11/2017 |
| CN | 107614670 | A | | 1/2018 |
| CN | 108102794 | A | | 6/2018 |
| CN | 108174855 | A | | 6/2018 |
| CN | 110903920 | A | | 3/2020 |
| DE | 10205134 | A1 | | 8/2003 |
| DE | 102005007293 | A1 | | 8/2006 |
| DE | 102006016575 | A1 | | 10/2007 |
| EP | 1102577 | A | | 5/2001 |
| EP | 1479377 | A1 | | 11/2004 |
| EP | 1577375 | A2 | | 9/2005 |
| EP | 3299446 | A1 | | 3/2018 |
| KR | 20130032927 | A | | 4/2013 |
| KR | 101425024 | B1 | | 8/2014 |
| WO | 2006-122103 | A1 | | 11/2006 |
| WO | 2013/013164 | A1 | | 1/2013 |
| WO | 2018/113643 | A1 | | 6/2018 |
| WO | 2018/125033 | A1 | | 7/2018 |
| WO | 2018-141074 | A1 | | 8/2018 |
| WO | 2019/018287 | A1 | | 1/2019 |
| WO | 2020/114679 | A1 | | 6/2020 |
| WO | 2020-214916 | A1 | | 10/2020 |

OTHER PUBLICATIONS

Non-final Rejection issued in corresponding U.S. Appl. No. 16/796,433, dated Jul. 9, 2021.
Final Rejection issued in corresponding U.S. Appl. No. 16/796,433, dated Dec. 21, 2021.
Office Action issued in corresponding DE Application No. 10 2020 001 131.4, dated Oct. 25, 2021 w/Machine English Translation.
Office Action issued in corresponding DE Application No. 10 2020 001 130.6, dated Oct. 19, 2021 w/Machine English Translation.
Notice of Allowance issued in corresponding U.S. Appl. No. 16/796,433, dated Apr. 20, 2022.
Examination report issued in corresponding AU Application No. 2020225452, dated Nov. 3, 2022.
Williams, R. 'Preservatives used in personal case products', The Australian Society of Cosmetic Chemists [retrieved from the Internet on Oct. 27, 2022] URL: https://ascc.com.au/preservatives-used-in-personal-care-products-2/Published Jan. 27, 2018.
Onza, Geogard Ultra™ [retrieved from the Internet on Oct. 27, 2022] URL: https://glenncorp.com/wp-content/uploads/2018/02/2017_10_Geogard-Ultra_TDS_d11_LowRes.pdf.
Office Action issued in corresponding Canadian Patent Application No. 3,130,958 dated Apr. 11, 2023.
Office Action issued in corresponding Chinese Patent Application No. 202080029924.8 dated Feb. 18, 2023.
Office Action issued in corresponding Chinese Patent Application No. 202080029960.4 dated Feb. 17, 2023.
"Safer Cosmetics for People in the EU", Summary of Regulation (EC) No. 1223/2009 on cosmetic products, 3 pages, downloaded Dec. 1, 2023 from Eur-Lex at https://eur-lex.europa.eu/legal-content/EN/TXT/?uri=LEGGISSUM:co0013&print=true.
"Luxurious Foaming Hand Soap" Product Specification Sheet CL-H0029, Edition Jun. 14, 2016, 1 page, Lubrizol Advanced Materials, Inc., Cleveland, OH US.
Foaming Liquid Hand Wash (SLES System), No. PHC-PF-18-093-001, Technical Data Sheet, 1 page, Chemrez Technologies, Inc., Quezon City, Philippines.
"Ingredients to Die For" Tech Sheet, 16 pages, https://ingredientstodiefor.com/ Ingredients To Die For,an Aroma Alternatives® Ltd. Co.
"Sodium Benzoate" Data Sheet, 4 pages, downloaded Dec. 1, 2023 from https://www.cosmeticsinfo.org/ingredient/sodium-benzoate/.
Office Action issued in corresponding Australian Patent Application No. 2023200033 dated Oct. 9, 2023.
Anderson, F. Alan, "Annual Review of Cosmetic Ingredient Safety Assessments: 2005/2006." Int'l. J. of Toxicology, 27 (Suppl. 1): 77-142 (2008) 66 pgs. Retrieved on May 9, 2024 from https://cir-reports.cir-safety.org/view-attachment/?id=e4ce160b-8e74-ec11-8943-0022482f06a6.
Aroma Alternatives Ltd Co. "Ingredients to Die For—Gluconolactone & Sodium Benzoate (GSB)." Product Catalog, Preservatives / Integrity Stabilizers and Certificate of Analysis, Cosmetics, 2 pages, 1999-2023. Retrieved on May 9, 2024 form https://www.ingredientstodiefor.com/item/Gluconolactone_Sodium_Benzoate_GSB_/565?category=32.
ashland.com—"euxyl™ k 500 preservative chemistry: antimicrobials—INCI/Chemical Name: Diazolidinyl Urea (and) Sodium Benzoate (and) Potassium Sorbate (and) Aqua (Water)." (2024) 3 pgs. Retrieved on May 9, 2024 from https://www.ashland.com/industries/personal-and-home-care/hair-care/euxyl-k-500-preservative.
European Commission—Health & Consumer Protection Directorate-General "Scientific Committee on Consumer Products (SCCP)—Opinion on Benzoic Acid and Sodium Benzoate." Adopted by the SCCP during 4th plenary of Jun. 21, 2005. 30 pgs. Retrieved on May 9, 2024 from https://ec.europa.eu/health/ph_risk/committees/04_sccp/docs/sccp_o_015.pdf.
Johnson, Jr., W. et al., "Safety Assessment of Benzyl Alcohol, Benzoic Acid and its Salts, and Benzyl Benzoate." Int'l. J. of Toxicology, vol. 36 (Suppl. 3) 2017, p. 5S-30S (26 pgs.). Retrieved on May 9, 2024 from https://cir-reports.cir-safety.org/view-attachment?id=d7068126-8d74-ec11-8943-0022482f06a6.
Joint Food and Agriculture Organization (FAO) Expert Committee on Food Additives—Toxicological Evaluation of Some Antimicrobials, Antioxidants, Emulsifiers, Stabilizers, Flour-Treatment Agents, Acids, and Bases. FOA Nutrition Meetings Report Series No. 40A, B, C (1965-1966) 3 pgs. Retrieved on May 9, 2024 from https://www.inchem.org/documents/jecfa/jecmono/40abcj02.htm.
Joint Food and Agriculture Organization (FAO)/World Health Organization (WHO) Expert Committee on Food Additives. "IPCS Inchem—Benzoic Acid"—Compendium Addendum 12/FNP 52 Add. 12/67 (2004). 2 pgs. Retrieved on May 9, 2024 from https://www.inchem.org/documents/jecfa/jeceval/jec_184.htm.
Liebert, M. A., et al., "Final Report on the Safety Assessment of Sorbic Acid and Potassium Sorbate." J. of the Amer. College of Toxicology. vol. 7, No. 6, pp. 837-880 (1988) 44 pgs. Retrieved on May 9, 2024 from https://cir-reports.cir-safety.org/view-attachment?id=d7068126-8d74-ec11-8943-0022482f06a6.
Liu, Chuang, "Household Detergents." Chemical Industry Press, p. 29, Jun. 30, 2001.
Ma, Jianzhong, "Synthesis Principles and Application Technologies of Leather Chemicals." Aug. 31, 2009, pp. 70 and 77, China.
Nair, Bindu, "Final Report on the Safety Assessment of Benzyl Alcohol, Benzoic Acid, and Sodium Benzoate." Int'l. J. of Toxicology, 20 (Suppl. 3) pp. 23-50 (2001) 28 pgs. Retrieved on May 9, 2024 from https://cir-reports.cir-safety.org/view-attachment?id=9a5e3329-8e74-ec11-8943-0022482f06a6.
Pilz, et al. "A Welcome Side Effect—How Velsan® SC (Sorbitan Caprylate) Helps Reduce the Concentration of Classical Preservatives." HPC (Household and Personal Care) Today Preservatives, Mar. 2010, pp. 22-26.
U.S.A. Government, Food & Drug Administration. "Code of Federal Regulations Title 21—Sodium Benzoate." Dec. 22, 2023 (last update); 2 pgs. Retrieved on May 9, 2024 from https://www.accessdata.fda.gov/scripts/cdrh/cfdocs/cfcfr/CFRSearch.cfm?fr=184.1733&SearchTerm=sodium%20benzoate.
U.S.A. Government, Food & Drug Administration. "Code of Federal Regulations Title 21—Benzoic Acid." Dec. 22, 2023 (last update); 2 pgs. Retrieved on May 9, 2024 from https://www.accessdata.fda.gov/scripts/cdrh/cfdocs/cfcfr/CFRSearch.cfm?fr=184.1021&SearchTerm=benzoic%20acid.

(56) References Cited

OTHER PUBLICATIONS

Wang, Duoren, "Organic Food Surfactants." Apr. 30, 2009, Science & Technology Lit Press, p. 139.
World Trade Organization (WHO) and European Commission, "IPCS Inchem—Benzoic Acid"—ICSC—0103 (Oct. 1999)—Case # 65-85-0, EC No. 200-618-2; 2 pgs. Retrieved on May 9, 2024 from https://www.inchem.org/documents/icsc/icsc/eics0103.htm.
EPO—European Examination Report mailed May 6, 2024 for corresponding European Application No. 20711735.9, 4 pgs.
KIPO—Korean Examination Report mailed May 11, 2024 for corresponding Korean Application No. 10-2021-7029516, 33 pgs.— Translation in English and Korean.
National Institute of Environmental Sciences. "Biocidal Substance— Guidelines for Preparation of Submissions for Approval of Biocides" (Publication Reg. No. 11-1480523-004445-01), Sep. 2021. NIER-GP2021-042; pp. 68-83, and 201 (total 30 pages). Only Korean translation.
'Flour', Wikipedia, 2000 [retrieved from the Internet on Aug. 31, 2022 (Aug. 31, 2022) at https://en.wikipedia.org/wiki/Flour] para 1.
'Thickening agent', Wikipedia, Aug. 31, 2022 {Aug. 31, 2022, date retrieved) [retrieved from the Internet on Aug. 31, 2022 (Aug. 31, 2022) at https://en.wikipedia.org/wiki/Thickening_agent] p. 2 para 7-8; p. 3 para 3.

\* cited by examiner

STABLE ANHYDROUS FOAMING AND GELLING HAND SOAP CONCENTRATE AND METHOD OF MAKING SAME

CROSS REFERENCE TO RELATED APPLICATIONS

This application claims priority to U.S. Provisional Application Nos. 62/808,021, filed Feb. 20, 2019, and 62/889,480, filed Aug. 20, 2019, the entire contents of which are incorporated by reference.

BACKGROUND

The majority of Hand Soap products come in as vessel with a dispenser. They also can come in as bulk as refill. These vessels are mostly plastic, glass, cardboard lined with plastic as water barrier. Majority of time these soap in the market are in thin liquid or gel forms. One of the problem is the packaging. Single use plastic is everywhere and it is wreaking havoc on the environment. Only 9% of all plastic is actually recycled, and packaging generates the largest portion of municipal waste (~30%). Packaged products are inefficient for businesses and the people who buy them.

Removing the water from Hand Soap formulations removes the need for single use plastic packaging and the waste that comes with it, such as packaging waste, product waste, and the waste of resources used to ship water.

Thus, a need exists for new stable formulations of hand soap concentrate that meet the needs of consumers, while also reducing the amount of waste generated in their production and shipping.

SUMMARY OF THE INVENTION

The invention relates to stable, anhydrous foaming and gelling hand soap concentrate formulations (also referred to as stable anhydrous hand soap concentrate formulations or concentrate formulations). The stable anhydrous hand soap concentrate formulations may be in a solid form such as a tablet, granulars, powder, sachet, or polymer membrane (PVA, PVP, HPMC, etc) form. The stable anhydrous hand soap concentrate formulation in a solid form can comprise a surfactant and a pH control agent. The stable anhydrous hand soap concentrate formulation in a solid form can further comprise an ingredient selected from a preservative, a preservative booster, a water softening agent, an emollient, a viscosity adjuster, an acidic cleaner, a basic cleaner, a thickening agent, and a binding agent. For example, the stable anhydrous hand soap concentrate formulation in a solid form can further comprise a preservative and a water softening agent. The stable anhydrous hand soap concentrate formulation in a solid form is substantially fatty acid free and/or substantially animal fat free.

In one aspect of the invention, a stable anhydrous foaming and gelling hand soap concentrate tablet (also referred to as foaming hand soap concentrate tablet) is provided. The foaming hand soap concentrate tablet of this disclosure may include an acidic cleaner, a binding agent, a surfactant, and optionally a pH control agent. The foaming hand soap concentrate tablet may or may not be substantially fatty acid free and/or substantially animal fat free.

In some embodiments, the foaming hand soap concentrate tablet is effervescent and comprises an acidic cleaner, a basic cleaner, a surfactant, a binding agent, and optionally an ingredient selected from a pH control agent, a water softening agent, a thickening agent and a coloring/dye agent, a preservative, a preservative booster, and a fragrance. The foaming hand soap concentrate tablet may have a pH of about 4.0 to about 6.0 when dissolved in appropriate amount of water. The foaming hand soap tablet may comprise citric acid, malic acid, sodium bicarbonate, sodium carbonate, sodium coco sulfate, dextrose, polyethylene glycol, a preservative, and medium chain triglyceride oil.

The foaming hand soap concentrate tablet may comprise one or more binding agents ranging from about 1% to about 20%, by weight.

The foaming hand soap concentrate tablet may comprise one or more acidic cleaner ranging from about 1.0% to about 85% by weight, based on the weight of the tablet.

In some embodiments, the foaming hand soap concentrate tablet may comprise an acidic cleaner in an amount ranging from about 1% to about 85% by weight, a pH control agent in an amount sufficient to adjust the pH to about 4.5 to about 5.5 when dissolved in appropriate amount of water, a chelating agent, a solvent (e.g., a binding agent), and an oily soil remover (e.g., a surfactant).

The foaming hand soap concentrate tablet further comprise a thickening agent. The foaming hand soap concentrate tablet further comprise a preservative booster. The foaming hand soap concentrate tablet further comprise a colorant and or a fragrance.

In some embodiments, the pH control agent is selected from the acidic cleaner and the basic cleaner. In some embodiments, the pH control agent is different from the acidic cleaner and/or the basic cleaner.

In some embodiments, the foaming hand soap concentrate tablet comprises a cleaner selected from acidic cleaners and basic cleaners, a surfactant, a binding agent, and optionally a pH control agent. The foaming hand soap concentrate tablet may have a pH of about 4.0 to about 6.0 when dissolved in appropriate amount of water. In some embodiments, the foaming hand soap concentrate tablet further comprises an ingredient selected from a pH control agent, a water softening agent, a thickening agent and a coloring/dye agent, a preservative, a preservative booster, and a fragrance. In some embodiments, the foaming hand soap concentrate tablet further comprises a thickening agent.

Although the embodiments above refer to the stable anhydrous hand soap concentrate formulations as tablets, they also apply to stable anhydrous hand soap concentrate formulations not in the form of tablets.

In one aspect of the invention a method of making a foaming hand soap concentrate tablet is provided.

DETAILED DESCRIPTION OF THE INVENTION

This disclosure relates to a stable, anhydrous hand soap concentrate formulation in a solid form. The inventors have discovered a solid formulation that is both good for the environment and effective for cleaning. The advantages of this anhydrous solid form over the traditional liquid cleansers include chemical stability, reduced packaging, and convenience for the consumer. The stable, anhydrous hand soap concentrate formulation can be in a tablet, granulars, powder, sachet, or polymer membrane (PVA, PVP, HPMC, etc) form.

As used in this specification, the singular forms "a," "an," and "the" include plural referents unless the context clearly dictates otherwise. Thus, for example, reference to a "preservative booster" includes a single kind of preservative booster or two or more different kinds of preservative booster.

"About" as used herein means within an acceptable error range for the particular value as determined by one of ordinary skill in the art, which will depend in part on how the value is measured or determined, (i.e., the limitations of the measurement system). For example, "about" can mean within 1 or more than 1 standard deviations, per practice in the art. Where particular values are described in the application and claims, unless otherwise stated, the term "about" means within an acceptable error range for the particular value. The term "about" when qualifying a value of a stated item, number, percentage, or term refers to a range of plus or minus ten percent of the value of the stated item, percentage, parameter, or term.

The term "anhydrous" as used herein refers to a stable, anhydrous hand soap concentrate formulation comprising less than about 5%, 4%, 3%, 2% or 1% by weight of water based on the weight of the concentrate formulation.

The term "substantially fatty acid-free" as used herein refers to a stable, anhydrous hand soap concentrate formulation comprising less than 10%, 9%, 8%, 7%, 6%, 5%, 4%, 3%, 2%, or 1% by weight of a fatty acid (or salt thereof) based on the weight of the concentrate formulation, or comprising a fatty acid (or salt thereof) in an amount less than the amount used in a hand soap bar.

The term "substantially animal fat free" as used herein refers to a stable, anhydrous hand soap concentrate formulation comprising less than 10%, 9%, 8%, 7%, 6%, 5%, 4%, 3%, 2%, or 1% by weight of an animal fat (such as tallow) (or salt thereof) based on the weight of the concentrate formulation, or comprising or comprising a an animal fat (or salt thereof) in an amount less than the amount used in a hand soap bar.

The term "water softening agent" as used herein may be used interchangeably with chelating agent. For example citric acid and ethylenediaminetetraacetic acid (EDTA) are examples of water softening agent.

Some of the ingredients may have multiple functions. However, when two or more ingredients defined based on their functions are included in a formulation disclosed herein, the ingredients differ from each other in terms of their chemical structure. For example citric acid can be a water softening agent and a acidic cleaner as well, but when both water softening agent and acidic cleaner are used in the description of the formulation, they intend to refer to different ingredients in terms of the chemical structure.

The term "comprising" includes the embodiments of "consisting of" or "consisting essentially of."

The stable anhydrous hand soap concentrate formulation in a solid form can comprise a surfactant and a pH control agent. The pH control agent is present in an amount greater than the amount of the surfactant. The stable anhydrous hand soap concentrate formulation in a solid form can further comprise an ingredient selected from a preservative, a preservative booster, a water softening agent, an emolient, a viscosity adjuster, an acidic cleaner, a basic cleaner, a thickening agent, and a binding agent. The stable anhydrous hand soap concentrate formulation in a solid form is substantially fatty acid free and/or substantially animal fat free.

In one aspect, a stable anhydrous foaming and gelling hand soap concentrate tablet (also referred to foaming hand soap concentrate tablet or stable anhydrous hand soap concentrate tablet) is provided. The foaming hand soap concentrate tablet of this disclosure may include an acidic cleaner, a binding agent, a surfactant, and optionally a pH control agent. The binding agent and the surfactant function as a solvent and oily soil remover, respectively, when the tablet is dissolved in water before use. The foaming hand soap concentrate tablet is substantially fatty acid free or substantially animal fat free. The effervescent ingredients (e.g., the acidic and basic cleaner) can facilitate homogeneous distribution and dissolution of the surfactant into water before use.

The embodiments described herein for foaming hand soap concentrate tablet can also apply to the stable anhydrous hand soap concentrate formulation in a solid form.

In some embodiments, the foaming hand soap concentrate tablet may further comprise a pH control agent.

In some embodiments, the foaming hand soap concentrate tablet may further comprise a chelating agent.

In some embodiments, the foaming hand soap concentrate tablet may further comprise a lubricating agent.

In some embodiments, the foaming hand soap concentrate tablet may further comprise a pH control agent, a chelating agent, and a lubricating agent.

In some embodiments, the foaming hand soap concentrate tablet may further comprise a carrier.

In some embodiments, the foaming hand soap concentrate tablet may further comprise a pH control agent, a chelating agent, a lubricating agent, and a carrier.

In some embodiments, the foaming hand soap concentrate tablet may further comprise a process aid/emollient.

In each of the preceeding embodiments, the foaming hand soap concentrate tablet may have a pH of about 4.0 to about 6.0 when dissolved in appropriate amount of water.

In each of the preceeding aspect or embodiments, the foaming hand soap concentrate tablet may further comprise a thickening agent. The thickening agent provides at least one of the desired lathering properties, viscosity properties, emollient properties, increased volume of foam, and retained foam formation.

In each of the preceeding aspect or embodiments, the foaming hand soap tablet may further comprise a basic cleaner.

In each of the preceeding aspect or embodiments, the foaming hand soap concentrate tablet may further comprise a preservative and optionally a preservative booster.

In each of the preceeding aspect or embodiments, the foaming hand soap concentrate tablet may further comprise a dye/colorant and optionally a fragrance.

In each of the preceeding aspect or embodiments, the foaming hand soap concentrate tablet may further comprise a water softening agent.

In each of the preceeding aspect or embodiments, the surfactant can be selected from non-ionic and anionic surfactants.

In some embodiments, the pH control agent is not the acidic or basic cleaner. When both an acidic or basic cleaner and a pH control agent are contained in a tablet, the acidic or basic cleaner differs from the pH control agent.

In some embodiments, the foaming hand soap concentrate tablet comprises a surfactant, a binding agent, a thickening agent, a preservative, a preservative booster, a cleaner, a process aid/emollient, and optionally a fragrance.

In some embodiments, the foaming hand soap concentrate tablet comprises citric acid, sodium coco sulfate, sodium carbonate, sodium benzoate, sodium alginate, PEG (polyethylene glycol such as PEG 8000), sorbitol crystalline p20, potassium sorbate, medium-chain triglycerides oil, and optionally a fragrance.

In some embodiments, the foaming hand soap concentrate tablet comprises a surfactant that is a combination of a nonionic surfactant and a nonionic surfactant, a binding agent, a cleaner, and optionally a colorant.

In some embodiments, the foaming hand soap concentrate tablet comprises citric acid, sodium carbonate, sodium lauryl sulfate, ethoxylated alcohol, PEG (such as PEG 8000), and optionally a colorant.

In some embodiments, the foaming hand soap tablet may include a pH control agent, an anionic surfactant, a binding agent, a preservative, and a lubricating agent. In some embodiments, the foaming hand soap tablet may include a pH control agent, non-ionic surfactant, a binding agent, a preservative, and a lubricating agent. The foaming hand soap tablet may have a pH of about 4.0 to about 6.0 when dissolved in appropriate amount of water. In one embodiment, the foaming hand soap tablet includes citric acid, malic acid, sodium bicarbonate, sodium coco sulfate, dextrose, polyethylene glycol, a preservative, and medium chain triglyceride oil powder. The foaming hand soap tablet may also include a fragrance.

In each of the preceeding embodiments or aspects, the tablet may further contain biologic cleaners, such as enzymes (e.g., protease, amylase, lipase, cellulose, pectinase, mannanase, and the like) and probiotics (e.g., lactobacillus, bifidobacterial, and the like). Biological cleaners may be present in an amount of about 0.01% to about 50% by weight, based on the weight of the tablet.

The amount of acidic cleaner in the tablet may range from about 1% to about 85%, from about 15% to about 20%, from about 20% to about 60%, from about 20% to about 45%, or from about 25% to about 35%, by weight, based on the weight of the tablet. The amount of acidic cleaner per tablet may be about 1%, about 5%, about 10%, about 15%, about 20%, about 25%, about 30%, about 35%, about 40%, about 50%, about 60%, about 70%, about 75%, about 80%, about 85%, about 5% to about 85%, about 10% to about 75%, about 15% to about 70%, about 20% to about 65%, about 25% to about 60%, about 30% to about 55%, about 35% to about 50%, or about 40% to about 45%. The acidic cleaner may be citric acid and/or malic acid.

The amount of the basic cleaner in the tablet may range from about 5% to about 40%, from about 5% to about 30%, from about 10% to about 30%, from about 10% to about 25%, from about 5% to about 10%, from about 40% to about 60%, or from about 35% to about 45%, by weight, based on the weight of the tablet. The amount of acidic cleaner per tablet may be about 5%, about 7%, about 9%, about 11%, about 13%, about 15%, about 17%, about 19%, about 21%, about 23%, about 25%, about 27%, about 29%, about 31%, about 33%, about 35%, about 37%, about 39%, or about 40%. The basic cleaner may be sodium carbonate, sodium bicarbonate and/or any other alkali carbonates.

The amount of the preservative in the tablet may range from about 5% to about 40%, from 5% to about 30%, from about 10% to about 30%, from about 10% to about 25%, or from about 10% to about 20%, by weight, based on the weight of the tablet. The amount of the preservative per tablet may be about 5%, about 7%, about 9%, about 11%, about 13%, about 15%, about 17%, about 19%, about 21%, about 23%, about 25%, about 27%, about 29%, about 31%, about 33%, about 35%, about 37%, about 39%, or about 40%. The preservative may be sodium benzoate, potassium sorbate, gluconolactone, and/or biocideal preservatives.

The amount of the preservative booster in the tablet may range from about 0.1% to about 10%, from about 0.5% to about 10%, from about 1% to about 10%, or from about 1% to about 5%, by weight, based on the weight of the tablet. The amount of the preservative booster per tablet may be about 0.1%, about 0.2%, about 0.3%, about 0.4%, about 0.5%, about 1%, about 2%, about 3%, about 4%, about 5%, about 6%, about 7%, about 8%, about 9%, or about 10%. The preservative booster may be a sorbate such as potassium sorbate.

The amount of the thickening agent in the tablet may range from about 1% to about 15%, from about 1% to about 10%, or from 5% to about 10%, by weight, based on the weight of the tablet. The amount of the thickening agent per tablet may be about 1%, about 2%, about 3%, about 4%, about 5%, about 6%, about 7%, about 8%, about 9%, about 10%, about 11%, about 12%, about 13%, about 14%, or about 15%, by weight, based on the weight of the tablet. The thickening agent may be xanthum gum (such as sodium alginate, alginate SS207), NaCl, KCl, potassium alginate, gura gum, and/or HPMC. Thickening agent can bring emollient properties and add body to the foam. Without thickening agent, the foam would go flat as the hands are rubbed for cleaning. Thickening agent can also provide the foam with paste like structure and when combined with surfactant it actually provides lathering properties and allows the foam to retain itself.

The pH of the tablet dissolved in water may range from about 4.5 to about 5.5. The pH of the tablet dissolved in appropriate amount of water may be about 4.5, about 5.0, or about 5.5. The pH may be adjusted by acidic or basic agent used in the tablet, such as the acidic cleaner and/or basic cleaner such as sodium carbonate or citric acid. The pH can also be adjusted by a pH control agent that differs from the acidic cleaner or basic cleaner contained in the tablet.

The pH control agent is in an amount sufficient to adjust the pH when dissolved in water from about 4.5 to about 5.5. When the pH control agent differs from the acidic or basic cleaner, its amount in the tablet ranges from about 5% to about 15%, such as from about 8% to about 12% by weight, based on the weight of the tablet. The pH control agent may be sodium metasilicate.

The amount of chelating agent in the tablet may range from about 0.01% to about 95% by weight, based on the weight of the tablet. The amount of chelating agent may be about 1%, about 1.5%, about 2.0%, about 2.5%, about 3.0%, about 3.5%, about 4.0%, about 4.5%, about 5.0%, about 5.5%, about 6.0%, about 6.5%, about 7.0%, about 7.5%, about 8.0%, about 8.5%, about 9.0%, about 9.5%, about 10.0%, about 2% to about 10.0%, about 3% to about 7%, or about 1% to about 10% by weight. The cleaning tablet may contain one or more chelating agents, such as MGDA (methylglycineadiacetic acid and salts), tri-sodium citrate, GLDA (L-glutamic acid, N, N-diacetic acid sodium salts), EDDS (ethylenediaminedisuccinic acid and salts), and IDS (iminodisuccinic acid and salts).

The amount of the binding agent in the tablet may range from about 0% to about 30% such as less than 5%, from about 0% to about 10%, from about 0% to about 20%, from about 3% to about 8%, from about 5% to about 15% by weight, based on the weight of the tablet. The amount of binding agent is suitable to form a tablet and may be about 1%, about 2%, about 3%, about 4%, about 5%, about 6%, about 7%, about 8%, about 9%, about 10%, about 12%, about 15%, about 18%, about 20%, about 3% to about 7%, about 4% to about 8%, about 5% to about 10%, or about 10% to about 20%. The binding agent may be selected from polyethylene glycol (e.g., polyethylene glycol 8000 such as T-Det® PEG 8000P) and sorbitol (such as sorbitol crystalline P20) and dextrose.

The amount of surfactant (i.e., oily soil remover) in the tablet may range from about 0.01% to about 40%, from about 1% to about 20%, from about 10% to about 20%, from about 10% to about 25%, from about 10% to about 40%, or from about 15% to about 25%, by weight, based on the weight of the tablet. The amount of oily soil remover may be about 1%, about 2%, about 3%, about 4%, about 5%, about 6%, about 7%, about 8%, about 9%, about 10%, about 12%, about 15%, about 18%, about 20%, about 16% to about 20%, about 3% to about 7%, about 4% to about 8%, about 8% to about 12%, about 5% to about 10%, about 10% to about 15%, or about 10% to about 20%. The surfactant can be natural or synthetic surfactants, such an anionic, non-ionic, amphoteric, zwitterionic, or cationic surfactants, such as anionic and non-ionic surfactants, further such as a surfactant selected from sodium coco sulfate, ethoxylated alcohols (such as ethoxylated alcohol C(10-12)-C(14-16) with 4-8 moles ethoxylation, for example Clariant Genapol LA 060 (ethoxylated alcohol C, 12-C, 16) w/6 moles ethoxylation, ethoxylated alcohols C8-C10 6-8 moles of EO, etc.), sodium lauryl sulfate, and alkyl polyglucosides (such as lauryl glucoside, caprylyl/myristyl glucoside, caprylyl/decyl Glucoside).

The amount of the process aid/emollient in the tablet may range from about 0.1% to about 1%, such as from about 0.1% to about 0.7%, further such as from about 0.2% to about 0.6% by weight, based on the weight of the tablet. The process aid/emollient can be selected from medium chain triglycerides with two or three fatty acids having an aliphatic tail of 6-12 carbon atoms, coconut fatty acid, coconut oil, glycerin, esters, and plant base oils.

The amount of the lubricating agent in the tablet may range from about 0.1 to about 2.0% by weight based on the weight of the tablet. Exemplary lubricating agent can be selected from magnesium stearate, leucine, sodium lauryl sulfate, sodium benzoate etc.

The amount of the carrier in the tablet may range from about 1% to about 10% by weight based on the weight of the tablet. Exemplary carrier can be selected from silicon dioxide.

The fragrance in the tablet may be natural fragrances (e.g., essential oils) and/or synthetic fragrances and perfumes in the form of oils, crystals, powders, granules, and encapsulations. The fragrance can be selected from fragrance clean basil.

The dye or coloring agent can be any of the Food, Drug and Cosmetic (FD&C) approved dyes and colorants.

The foaming hand soap concentrate tablet may also be formulated in the form of a sheet.

The foaming hand soap concentrate tablet can be in any size. For example, the tablet can be in any size that when dissolved into 12 oz or less amount of water, a fully functional foaming hand soap for multiple use is formed. The tablet may weigh from about 5.0 to about grams 15 grams, from about 8.2 to about 8.8 grams, such as about 8.5 grams and dissolved into about 7 to 10 oz, such as about 9 oz, of water before use.

To avoid effervescence from happening during storage when the tablets contain both an acidic and basic cleaner, the tablet can have a sufficient hardness and/or the tablet contains a desiccating agent such as hydrated silica or any other agent known to absorb moisture.

Methods for Preparing Stable Anhydrous Hand Soap Concentrate Tablets

The stable anhydrous hand soap tablets can be prepared using any suitable method. Stable anhydrous Hand Soap cleanser tablet can be prepared using direct compression or wet granulation process. For this application direct compression is most preferred. The term direct compression (or direct compaction) is used to define the process by which tablets are compressed directly from powdered mixture of ingredients into a firm compact without employing the process of granulation. Powder is blended homogeneously by using a blender (Ribbon Blender, V-blender, paddle blender, drum mixing). The powder blender is then charged into the hopper of tablet press. Desire weight, compression ton, & hardness of tablet are set as the tablets get compressed and come out of the tablet press.

Formats

Although described throughout the application as tablets, the stable anhydrous hand soap concentrate formulations may be formatted as tablets, powders, granules, sachets, packs, polymer membrane (natural or syntactic) and sheets. The stable anhydrous hand soap concentrate formulations may also be formatted in single-use sheets.

The hand soap formulations described herein may be designed to be rinsed off, wiped, off, or left off for maximum cleaning efficiency.

In a preferred embodiment, the tablets are round, however other geometric shapes are contemplated.

Methods of Using Stable Anhydrous Cleanser Tablets

In one aspect, the invention includes a method of using any of the tablets described herein including the steps of (1) filling a bottle or vessel with water, (2) adding a hand soap tablet to the water-filled bottle or vessel, and (3) dissolving the tablet in water by stirring or shaking.

For example, the method of using the effervescent tablet comprises (1) filling a foaming hand soap vessel with water, cold, warm, or hot, (2) add one tablet into the vessel, and (3) placing a foaming pump on the vessel, and (4) dispensing the content in the vessel after the tablet is substantially dissolved.

Each individual hand soap tablet, when exposed to water and stirred or shaken, will dissolve into a liquid cleansing solution. Upon experiencing dissolution of the cleanser tablet, the user may proceed with cleaning or washing as usual. Individual tablets may be packaged together in suitable bulk quantities.

The hand soap tablets may be stored in any suitable container, such as but not limited to plastic, glass, aluminum, ceramic, or acrylic container. The container may contain a desiccant. The container may be re-usable and refilled with new tablets as needed.

One set of non-limiting exemplary embodiments are disclosed below:

1. A stable anhydrous hand soap concentrate formulation in a solid form, comprising a surfactant and a pH control agent, wherein the stable anhydrous hand soap concentrate formulation is substantially fatty acid free and/or substantially animal fat free.
2. The stable anhydrous hand soap concentrate formulation of embodiment 1, wherein the pH control agent is present in an amount that is greater than the amount of the surfactant.
3. The stable anhydrous hand soap concentrate formulation of embodiment 1 or 2, wherein the pH control agent is present in an amount ranging from 1% to about 85%, from about 15% to about 20%, from about 20% to about 60%, from about 20% to about 45%, from about 25% to about 35%, from 5% to about 40%, from about 5% to about 30%, from about 10% to about 30%, from about 10% to about 25%, from about 5% to about 10%, from about 40% to about 60%, from about 35% to about 45%, from about 30% to about 55%, or from about 35% to about 55%, by weight, based on the weight of the formulation.
4. The stable anhydrous hand soap concentrate formulation of any of embodiments 1-3, wherein the surfactant is present in an amount ranging from about 0.01% to about 40%, from about 1% to about 20%, from about 10% to about 20%, from about 10% to about 25%, from about 10% to about 40%, from about 5% to about 15%, from about 5% to about 25%, or from about 15% to about 25%, by weight, based on the weight of the formulation.

5. The stable anhydrous hand soap concentrate formulation of any of embodiments 1-4, wherein the surfactant comprises an anionic and/or nonionic surfactant.

6. The stable anhydrous hand soap concentrate formulation of embodiment 5, wherein the anionic surfactant is selected from sodium coco sulfate and sodium lauryl sulfate.

7. The stable anhydrous hand soap concentrate formulation of embodiment 5 or 6, wherein the nonionic surfactant is selected from ethoxylated alcohol and alkyl polyglucosides.

8. The stable anhydrous hand soap concentrate formulation of any of embodiments 1-7, wherein the pH control agent comprises an acidic cleaner.

9. The stable anhydrous hand soap concentrate formulation of any of c embodiments 1-7, wherein the pH control agent comprises a basic cleaner.

10. The stable anhydrous hand soap concentrate formulation of any of embodiments 1-7, wherein the pH control agent comprises an acidic cleaner and a basic cleaner.

11. The stable anhydrous hand soap concentrate formulation of embodiment 8 or 10, wherein the acidic cleaner is selected from citric acid and malic acid.

12. The stable anhydrous hand soap concentrate formulation of any of embodiments 9-11, wherein the basic cleaner is selected from sodium carbonate, sodium bicarbonate and any other alkali carbonates.

13. The stable anhydrous hand soap concentrate formulation of any of embodiments 1-12, further comprising a binding agent.

14. The stable anhydrous hand soap concentrate formulation of embodiment 13, wherein the binding agent is present in an amount ranging from 0% to about 30%, less than 5%, from about 0% to about 10%, from about 0% to about 20%, from about 3% to about 8%, from about 5% to about 15% by weight, based on the weight of the formulation.

15. The stable anhydrous hand soap concentrate formulation of embodiment 13 or 14, wherein the binding agent is selected from polyethylene glycol, sorbitol, and dextrose.

16. The stable anhydrous hand soap concentrate formulation of any of embodiments 1-15, further comprising a thickening agent.

17. The stable anhydrous hand soap concentrate formulation of embodiment 16, wherein the thickening agent is present in an amount ranging from about 1% to about 15%, from about 1% to about 10%, or from 5% to about 10%, by weight, based on the weight of the formulation.

18. The stable anhydrous hand soap concentrate formulation of embodiment 16 or 17, wherein the thickening agent is selected from xanthum gum, NaCl, KCl, potassium alginate, gura gum, and HPMC.

19. The stable anhydrous hand soap concentrate formulation of any of embodiments 1-18, further comprising a preservative and/or preservative booster.

20. The stable anhydrous hand soap concentrate formulation of embodiment 19, wherein the preservative is present in an amount ranging from 5% to about 40%, from 5% to about 30%, from about 10% to about 30%, from about 10% to about 25%, or from about 10% to about 20%, by weight, based on the weight of the formulation.

21. The stable anhydrous hand soap concentrate formulation of embodiment 19 or 20, wherein the preservative booster is present in an amount ranging from about 0.1% to about 10%, from about 0.5% to about 10%, from about 1% to about 10%, or from about 1% to about 5%, by weight, based on the weight of the formulation.

22. The stable anhydrous hand soap concentrate formulation of any of embodiments 19-21, wherein the preservative is selected from sodium benzoate, gluconolactone, and biocideal preservatives.

23. The stable anhydrous hand soap concentrate formulation of any of embodiments 19-22, wherein the preservative booster is selected from sorbate.

24. The stable anhydrous hand soap concentrate formulation of any of embodiments 1-23, further comprising an ingredient selected from process aid, fragrance, chelating agent, lubricating agent, and a coloring agent.

25. The stable anhydrous hand soap concentrate formulation of any of embodiments 1-24, wherein said formulation produces a low pH solution in the range of about 4.0 to about 6.0 when dissolved in appropriate amount of water 26. The stable anhydrous hand soap concentrate formulation of any of embodiments 1-25, comprising citric acid, sodium carbonate, sodium lauryl sulfate, ethoxylated alcohol, polyethylene glycol, and optionally a coloring agent.

27. The stable anhydrous hand soap concentrate formulation of any of embodiments 1-25, comprising citric acid, sodium carbonate, sodium coco sulfate, sodium benzoate, sodium alginate, polyethylene glycol, sorbitol, medium-chain triglycerides oil, and a fragrance.

28. The stable anhydrous hand soap concentrate formulation of any of embodiments 1-27, which is in the form of a tablet.

29. The stable anhydrous hand soap concentrate formulation of embodiment 28, which is in the form of a tablet wherein the tablet is not tacky.

30. A method of preparing a tablet, comprising blending homogeneously the ingredients of any of embodiments 1-28 to form a mixture and compressing the mixture to form the tablet.

31. A method of using the tablet of embodiment 29 comprising (1) filling a bottle or vessel with water, (2) adding the tablet to the water-filled bottle or vessel, and (3) dissolving the tablet in appropriate amount of water.

Another set of non-limiting exemplary embodiments are disclosed below:

1. A stable anhydrous hand soap concentrate formulation in a solid form, comprising a surfactant and a pH control agent, wherein the stable anhydrous hand soap concentrate formulation is substantially fatty acid free and/or substantially animal fat free.

2. The stable anhydrous hand soap concentrate formulation of embodiment 1, further comprising an ingredient selected from a preservative, a preservative booster, a water softening agent, an emolient, a viscosity adjuster, an acidic cleaner, a basic cleaner, a thickening agent, and a binding agent.

3. The stable anhydrous hand soap concentrate formulation of embodiment 2, wherein the ingredient is selected from preservative and a water softening agent.

4. A stable and anhydrous foaming hand soap concentrate tablet, comprising an acidic cleaner, a binding agent, and a surfactant.

5. The tablet of embodiment 4, further comprising a pH control agent and a chelating agent.

6 The tablet of embodiment 5, further comprising at least one natural and/or synthetic fragrance.

7. The tablet of embodiment 5 or 6, further comprising a dye or coloring agent.

8. The tablet of any of embodiments 4-6, wherein said tablet produces a low pH solution in the range of about 4.0 to about 6.0 when dissolved in appropriate amount of water.

9. The tablet of embodiment 4, comprising an acidic cleaner, a pH control agent, a binding agent, a surfactant, a preservative and a lubricating agent.

10. The tablet of embodiment 4, comprising an acidic cleaner, a pH control agent, an anionic surfactant, a binding agent, a preservative and a lubricating agent.

11 The tablet of embodiment 4, comprising an acidic cleaner, a pH control agent, a non-ionic surfactant, a binding agent, and a lubricating agent.

12. The tablet of embodiment 11, wherein said tablet produces a solution having a pH of about 4.0 to about 6.0 when dissolved in appropriate amount of water.

13. The tablet of embodiments 4, wherein said tablet comprises citric acid, malic acid, sodium bicarbonate, sodium coco sulfate, dextrose, polyethylene glycol, a preservative, and medium chain triglyceride oil liquid.

14 The tablet of embodiments 11 or 12, comprising citric acid, sodium bicarbonate, ethoxylated alcohol, polyethylene glycol, and magnesium stearate.

15. The foaming hand soap concentrate tablet of any one of embodiments 10-14, further comprising a fragrance.

16. The tablet of any of embodiments 4-12, further comprising a basic cleaner to form a effervescent tablet.

17. The tablet of embodiment 16, further comprising a thickening agent.

18 The tablet of embodiment 17, wherein the thickening agent is selected from sodium alginate, potassium alginate, and HMPC.

19 The tablet of embodiment 17 or 18, further comprising a preservative and optionally a preservative booster.

20. The tablet of embodiment 19, further comprising a process aid/emollient.

21. The tablet of embodiment 20, comprising citric acid, sodium carbonate, sodium coco sulfate, sodium benzoate, sodium alginate, polyethylene glycol, sorbitol, a preservative booster, a fragrance, and medium chain triglyserides.

22 The tablet of any one of embodiments 4-21, wherein the binding agent ranges from about 1% to about 20% by weight.

23. The tablet of any one of embodiments 4-21, wherein the amount of acidic cleaner ranges from about 1.0% to about 85% by weight, based on the weight of the tablet.

24. A stable and anhydrous foaming hand soap concentrate tablet for use in cleaning hand, comprising, an acidic cleaner in an amount ranging from about 1% to about 85% by weight, a pH control agent in an amount sufficient to adjust the pH to about 4.5 to about 5.5 when dissolved in appropriate amount of water, a chelating agent, a binding agent, and surfactant.

25. A method of using the tablet of any one of embodiments 4-30 comprising (1) filling a spray bottle with water. (2) adding the tablet to the water-filled spray bottle, and (3) dissolving the tablet in appropriate amount of water.

EXEMPLIFICATION

Materials used in the following Examples and their sources are listed below.

Example 1

A foaming hand soap tablet wag produced, using the following ingredients:

TABLE 1

| Raw Materials | Chemistry | Function in tablet | Function in final dilution | Weight (%) |
|---|---|---|---|---|
| Citric Acid | Citric Acid | Acid for effervescent | pH control | 20-30% |
| Sodium Carbonate | Sodium Carbonate Dense | Base for effervescent | Cleaner/pH control | 10-25% |
| Sodium Lauryl Sulfate | Sodium Lauryl Sulfate | Anionic Surfactant | Soil remover | 5-25% |
| BASF Lutensol AT 25 | ethoxylated alcohols | Nonionic Surfactant | oily soil remover | 5-15% |
| PEG 8000 | Polyethylene Glycol 8000 | Binder | solvent | <5% |
| Fragrance | n/a | sensorial effect | sensorial effect | 1-3% |
| Dye/colorant | FD&C or polymetric dye | visual effect | visual effect | 0.001-0.01 |
| Total | | | | 100 |
| pH | | | | pH 4.0-6.0 |
| Liquid Load (%) | | | | 3 |

Example 2

A foaming hand soap tablet was produced, using the following ingredients:

TABLE 2

| Raw Materials | Chemistry | Function in tablet | Function in final dilution | Weight (%) |
|---|---|---|---|---|
| Citric Acid | Citric Acid | Acid for effervescent | pH control | 25-35 |
| Sodium Coco Sulfate | Sodium Coco Sulfate | Surfactant | oily soil remover | 10-25 |
| Sodium Carbonate | Sodium Carbonate Dense | Base for effervescent | Cleaner/pH control | 10-20 |
| Sodium Benzoate | Sodium Benzoate | Lubricating/ Preservative | Preservative | 10-30 |
| Sodium Alginate (Alginate SS207) | Sodium Alginate ( | Thickening Agent | emollient | 1-10 |
| PEG 8000 | Polyethylene Glycol 8000 | Binder | solvent | 0-20 |
| Sorbitol Crystalline P20 | Sorbitol | Binder | solvent | 0-10 |
| Potassium Sorbate | Potassium Sorbate | preservative booster | Preservative | 1-10 |
| Fragrance Clean Basil | Fragrance Clean Basil | sensorial effect | sensorial effect | 0-2 |
| Medium-chain triglycerides Oil | Medium-chain triglycerides Oil | Process aid/emollient | emollient | 0.2-0.6 |
| Total | | | | 100.00 |
| pH | | | | 4.0-6.0 when dissolved in water |

One tablet is dissolved into about 9 oz of water.

The cleaning performance of the hand soap formulation described herein are tested using a blind consumer panel. The cleaning efficieny of the hand soap formulation described herein are satisfactory and comparable to that of standard such as dial in terms of cleaning, lathering, rinse off, hand feel, and/or dryness.

The invention claimed is:

1. A stable anhydrous hand soap concentrate formulation in a solid form, comprising a first surfactant, a first preservative, a second preservative, sodium alginate, polyethylene glycol, sorbitol, a medium-chain triglyceride oil, a fragrance, and a pH control agent,
   wherein the pH control agent comprises an acidic cleaner and a basic cleaner,
   wherein the acidic cleaner is citric acid and the basic cleaner is sodium carbonate,
   wherein the medium-chain triglycerides comprise aliphatic tails of 6-12 carbon atoms,
   wherein the percentage by weight for the second preservative is at least about 6% based on the weight of the stable anhydrous hand soap concentrate formulation,
   wherein the total combined percentage by weight for the first preservative and the second preservative is from about 6% to about 40% based on the weight of the stable anhydrous hand soap concentrate formulation,
   wherein the percentage by weight of the first preservative based on the weight of the stable anhydrous hand soap concentrate formulation is less than or equal to the percentage by weight of the second preservative based on the weight of the stable anhydrous hand soap concentrate formulation,
   wherein the first preservative is potassium sorbate, and wherein the second preservative is sodium benzoate,
   wherein the stable anhydrous hand soap concentrate formulation is substantially fatty acid free and/or substantially animal fat free,
   wherein the stable anhydrous hand soap concentrate formulation weighs from about 5.0 grams to about 15.0 grams,
   wherein the stable anhydrous hand soap concentrate formulation if dissolved in an amount of water would produce a solution,
   wherein the amount of water is from about 7 ounces to about 10 ounces, and
   wherein the pH of the solution is from about 4.0 to about 6.0.

2. The stable anhydrous hand soap concentrate formulation of claim 1, wherein the pH control agent is present in an amount that is greater than the amount of the first surfactant.

3. The stable anhydrous hand soap concentrate formulation of claim 1, wherein the pH control agent is present in an amount ranging from 1% to about 85%, from about 15% to about 20%, from about 20% to about 60%, from about 20% to about 45%, from about 25% to about 35%, from about 5% to about 40%, from about 5% to about 30%, from about 10% to about 30%, from about 10% to about 25%, from about 5% to about 10%, from about 40% to about 60%, from about 35% to about 45%, from about 30% to about 55%, or from about 35% to about 55%, by weight, based on the weight of the stable anhydrous hand soap concentrate formulation.

4. The stable anhydrous hand soap concentrate formulation of claim 1, further comprising a second surfactant.

5. The stable anhydrous hand soap concentrate formulation of claim 4, wherein the second surfactant is selected from ethoxylated alcohol, alkyl polyglucosides, and sodium lauryl sulfate.

6. The stable anhydrous hand soap concentrate formulation of claim 1, further comprising a binding agent.

7. The stable anhydrous hand soap concentrate formulation of claim 6, wherein the binding agent is present in an amount ranging from about 0% to about 30%, less than 5%, from about 0% to about 10%, from about 0% to about 20%, from about 3% to about 8%, or from about 5% to about 15% by weight, based on the weight of the stable anhydrous hand soap concentrate formulation.

8. The stable anhydrous hand soap concentrate formulation of claim 6, wherein the binding agent is dextrose.

9. The stable anhydrous hand soap concentrate formulation of claim 1, further comprising a thickening agent.

10. The stable anhydrous hand soap concentrate formulation of claim 9, wherein the thickening agent is present in an amount ranging from about 1% to about 15%, from about 1% to about 10%, or from about 5% to about 10%, by weight, based on the weight of the stable anhydrous hand soap concentrate formulation.

11. The stable anhydrous hand soap concentrate formulation of claim 1, further comprising a preservative booster.

12. The stable anhydrous hand soap concentrate formulation of claim 11, wherein the preservative booster is present in an amount ranging from about 0.1% to about 10%, from about 0.5% to about 10%, from about 1% to about 10%, or from about 1% to about 5%, by weight, based on the weight of the stable anhydrous hand soap concentrate formulation.

13. The stable anhydrous hand soap concentrate formulation of claim 1, further comprising an ingredient selected from a process aid, a chelating agent, a lubricating agent, and a coloring agent.

14. The stable anhydrous hand soap concentrate formulation of claim 1, further comprising sodium lauryl sulfate, ethoxylated alcohol, and optionally a coloring agent.

15. The stable anhydrous hand soap concentrate formulation of claim 1, wherein the solid form is a tablet.

16. The stable anhydrous hand soap concentrate formulation of claim 15, wherein the tablet is not tacky.

17. A method of preparing a tablet, comprising blending homogeneously the ingredients of claim 1 to form a mixture and compressing the mixture to form the tablet.

18. A method of using the tablet of claim 16, comprising (1) filling a bottle or a vessel with the amount of water, (2) adding the tablet to the bottle or the vessel, and (3) dissolving the tablet in the amount of water.

19. A method of dissolving the stable anhydrous hand soap concentrate formulation of claim 1 to produce the solution, the method of dissolving the stable anhydrous hand soap concentrate formulation to produce the solution comprising dissolving the stable anhydrous hand soap concentrate formulation in the amount of water to produce the solution.

20. The solution produced by the method of claim 19, wherein the amount of water is from about 7 ounces to about 10 ounces, and wherein the pH of the solution is from about 4.0 to about 6.0.

21. The stable anhydrous hand soap concentrate formulation of claim 1, wherein the first surfactant is present in an amount ranging from about 10% to about 40%.

22. The stable anhydrous hand soap concentrate formulation of claim 1, wherein the first surfactant is selected from sodium coco sulfate and sodium lauryl sulfate.

* * * * *